US008994948B2

(12) United States Patent
Tondello

(10) Patent No.: US 8,994,948 B2
(45) Date of Patent: Mar. 31, 2015

(54) APPARATUS FOR THE NON-DESTRUCTIVE TESTING OF THE INTEGRITY AND/OR SUITABILITY OF SEALED PACKAGINGS

(71) Applicant: L Pro S.R.L., Padua (IT)

(72) Inventor: Giuseppe Tondello, Padua (IT)

(73) Assignee: L Pro S.R.L., Padua (PD) (IT)

( * ) Notice: Subject to any disclaimer, the term of this patent is extended or adjusted under 35 U.S.C. 154(b) by 21 days.

(21) Appl. No.: 13/845,006

(22) Filed: Mar. 17, 2013

(65) Prior Publication Data

US 2013/0258346 A1 Oct. 3, 2013

(30) Foreign Application Priority Data

Mar. 27, 2012 (IT) .............................. M12012A0493

(51) Int. Cl.
G01N 21/31 (2006.01)
G01N 21/3504 (2014.01)
G01N 21/359 (2014.01)

(52) U.S. Cl.
CPC ............ *G01N 21/31* (2013.01); *G01N 21/3504* (2013.01); *G01N 21/359* (2013.01)
USPC ........................................................ 356/437

(58) Field of Classification Search
USPC ................................................. 356/432–440
See application file for complete search history.

(56) References Cited

U.S. PATENT DOCUMENTS 4,555,627 A * 11/1985 McRae, Jr. ..................... 250/334
5,298,751 A * 3/1994 Fee et al. .................... 250/338.5
6,639,678 B1 * 10/2003 Veale ............................. 356/437
8,638,439 B2 * 1/2014 Svanberg et al. .............. 356/437
2004/0263852 A1 * 12/2004 Degtiarev et al. ............. 356/437
2006/0203248 A1 * 9/2006 Reichardt et al. ............. 356/437
2011/0013009 A1 1/2011 Ramel
2011/0134431 A1 6/2011 Yokobayashi

FOREIGN PATENT DOCUMENTS

WO 2012001633 A2 1/2012

OTHER PUBLICATIONS

Italian Search Report IT MI20120493 Dated Nov. 19, 2012.

* cited by examiner

*Primary Examiner* — Hoa Pham
(74) *Attorney, Agent, or Firm* — Hedman & Costigan, P.C.; James V. Costigan; Kathleen A. Costigan

(57) ABSTRACT

An apparatus for the non-destructive testing of the integrity and/or suitability of sealed packagings having at least one portion (111,121) at least partially optically transparent, preferably food packagings, in particular through a verification of conformity of the atmosphere inside such food packagings, wherein the apparatus comprises at least one inspection area (20); at least one laser source (11) with an optical axis (A); at least one detector (13) positioned so as to detect at least one portion of back-scattered beams (12') following the collision of the laser beam (12) emitted by the laser source (11) with a target (100,200) and provide—at the output—a representative datum of an absorption spectrum of the gas. The apparatus includes means for measuring a distance covered by the laser beam (12) and electronic processing means for calculating the concentration of the gas.

12 Claims, 4 Drawing Sheets

APPARATUS FOR THE NON-DESTRUCTIVE TESTING OF THE INTEGRITY AND/OR SUITABILITY OF SEALED PACKAGINGS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISK

Not Applicable

REFERENCE TO A MICROFICHE APPENDIX

Not Applicable

BACKGROUND OF THE INVENTION

1. Field of the Invention

The present invention refers to an apparatus for the non-destructive testing of the integrity and/or suitability of sealed packagings, preferably food packagings, in particular through a verification of conformity of the atmosphere inside such food packagings.

2. Description of Related Art

Regarding the preservation of food products there is known the packaging in modified atmosphere, i.e. in sealed packagings filled with a determined gas or mixture of gases capable of preserving the food products therein, maintaining the organoleptic properties thereof substantially unaltered. Such packagings are known by the MAP (Modified Atmosphere Packaging) acronym.

In particular, regarding the correct preservation of food, the content of oxygen present in the packaging is of great importance. Specifically, regarding each food product, the correct preservation is obtained by means of a characteristic concentration of oxygen.

Generally there is the tendency of reducing the amount of oxygen with respect to the one present naturally in the atmosphere, for example replacing it with carbon dioxide or nitrogen, as the degradation of food is mainly due to the presence of oxygen in the packaging which causes the oxidation of various proteins widely present in most food products.

An exception is however represented by meat, especially minced or sausages, in which in order to heighten the red colour, there is introduced a higher amount of oxygen with respect to that present in the atmosphere. Therefore, there definitely arises the need of being able to monitor the concentration of gases inside the packagings, in particular of the food product type, with the aim of verifying the maintenance of the nominal characteristics.

Thus, besides identifying food packagings with mixtures of gases not meeting the desired standards, for example due to incorrect filling thereof, it is also possible to identify packagings not sealed correctly, thus in which the mixture of gases is similar to that of the external atmosphere.

Currently it is known to verify the concentration of a gas inside a sealed food packaging by collecting—using a syringe—a sample of the mixture of gases inside such container and analysing it with a suitable sensor of the contact type such as an electro-chemical sensor or the like, such as for example a lambda probe. Such measurements, though providing reliable results, reveal considerable drawbacks of use due to the complexity and the times required for performing the test, as well as the fact that, in order to collect the sample of the mixture of gases inside a sealed packaging, such packaging is irremediably jeopardised thus not being suitable for re-introduction into the production line.

This makes such measurements suitable for solely sample testing, thus definitely excluding the possibility of their use in line with the aim of performing a test on the entirety of the produced packagings.

Furthermore, there is known a system for non-destructive testing of the integrity and suitability of sealed food packagings described in the International patent application WO 2010/145892.

Such system measures, through laser spectroscopy, the radiation portion of the diffusive type which exits from a food packaging, after sending a laser radiation thereinto.

According to such measurement there is determined the absorption of the radiation operated by a determined gas present in the packaging which, compared with an expected absorption value, provides an indication in relation with a possible alteration of the concentration of such gas.

Thus, the system described in WO 2010/145892 is not capable of providing an absolute measurement of the concentration of the measured gas, thus leading to the need of providing a specific reference for each type of packaging and food product contained therein.

Furthermore, there is known another laser spectroscopy system used in particular for the non-destructive testing of the integrity and suitability of sealed food packagings filled with liquids where it is assumed that the water vapour is in saturation and the value thereof is thus a function of the temperature alone.

Such system provides alongside the measurement of the gas intended to be monitored a second measurement channel based on the measurement of the water vapour. Thus, such second measurement channel provides a reference from which the absolute measurement of the gas to be monitored is derived.

It is clear that the need for a second measurement channel makes the apparatus complex and expensive. Furthermore, such known apparatus cannot be used in packagings containing solid food products.

BRIEF SUMMARY OF THE INVENTION

An object of the present invention is to overcome the aforementioned drawbacks and in particular it is that of designing an apparatus for the non-destructive testing of the integrity and/or suitability of sealed packagings that is capable of providing an absolute measurement of the concentration of a gas inside a packaging, regardless of the particular configuration thereof.

Another object of the present invention is to provide an apparatus for the non-destructive testing of the integrity and/or suitability of sealed packagings that can be applied both for testing packagings containing liquids and for testing packagings containing solids.

A further object of the present invention is to provide an apparatus for the non-destructive testing of the integrity and/or suitability of sealed packagings that is capable of providing reliable results but without altering the integrity of the packaging.

Last but not least, an object of the present invention is to provide an apparatus for the non-destructive testing of the integrity and/or suitability of sealed packagings which can be used for an in line testing.

These and other objects according to the present invention are attained by providing an apparatus for the non-destructive testing of the integrity and/or suitability of sealed packages as described herein.

Further characteristics of the apparatus for the non-destructive testing of the integrity and/or suitability of sealed packagings are an object of the dependent claims.

BRIEF DESCRIPTION OF THE SEVERAL VIEWS OF THE DRAWINGS

The characteristics and the advantages of an apparatus for the non-destructive testing of the integrity and/or suitability of sealed packagings according to the present invention will be clearer from the following exemplifying and non-limiting description with reference to the attached schematic drawings wherein.

With reference to the figures, there is shown an apparatus for the non-destructive testing of the integrity and/or suitability of sealed packagings 100, indicated in its entirety with 10.

DETAILED DESCRIPTION OF THE INVENTION

Figure 1:
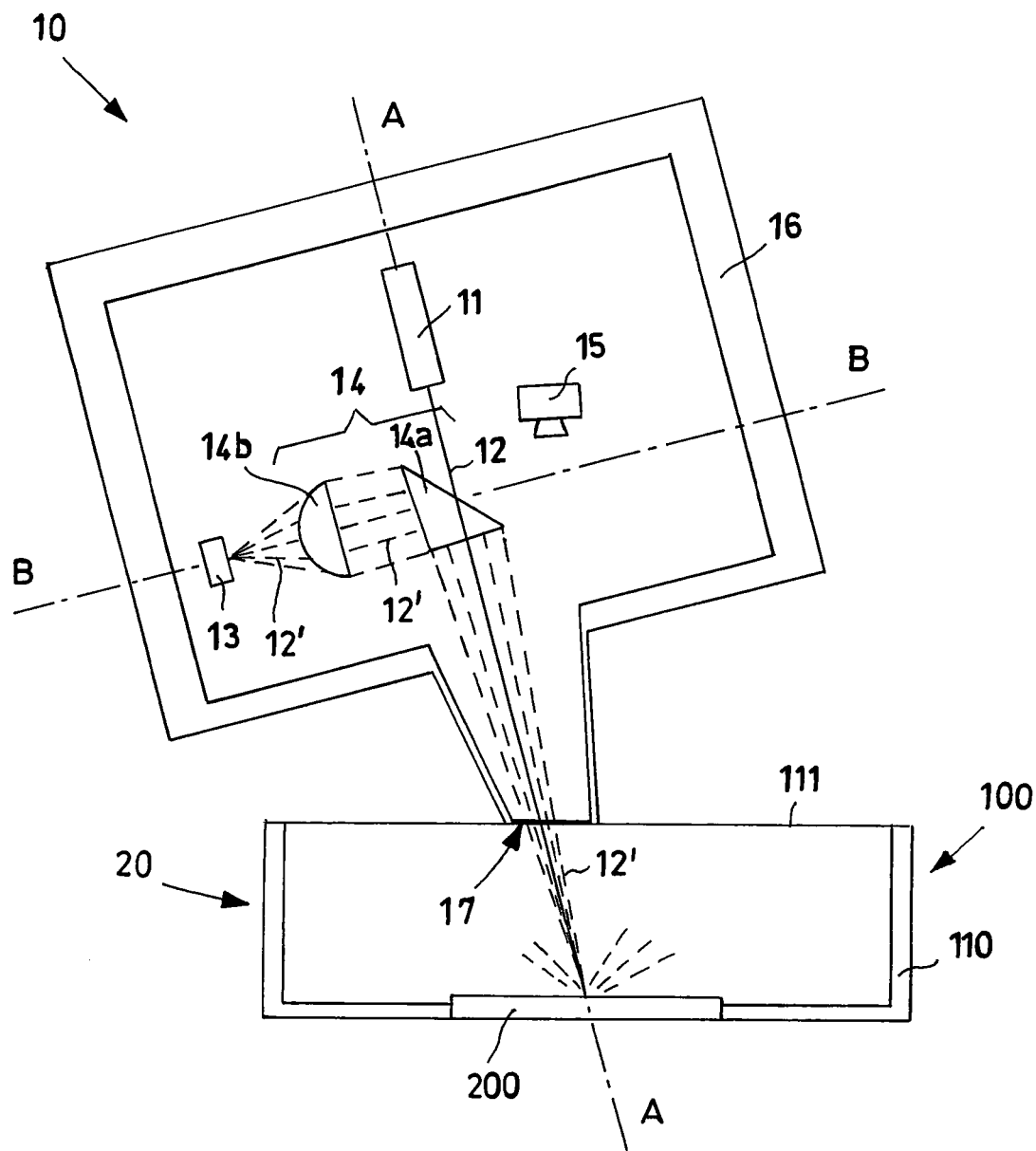
FIG. 1 is a schematic view of a preferred embodiment of an apparatus for the non-destructive testing of the integrity and/or suitability of sealed packagings according to the present invention.
Figure 2:
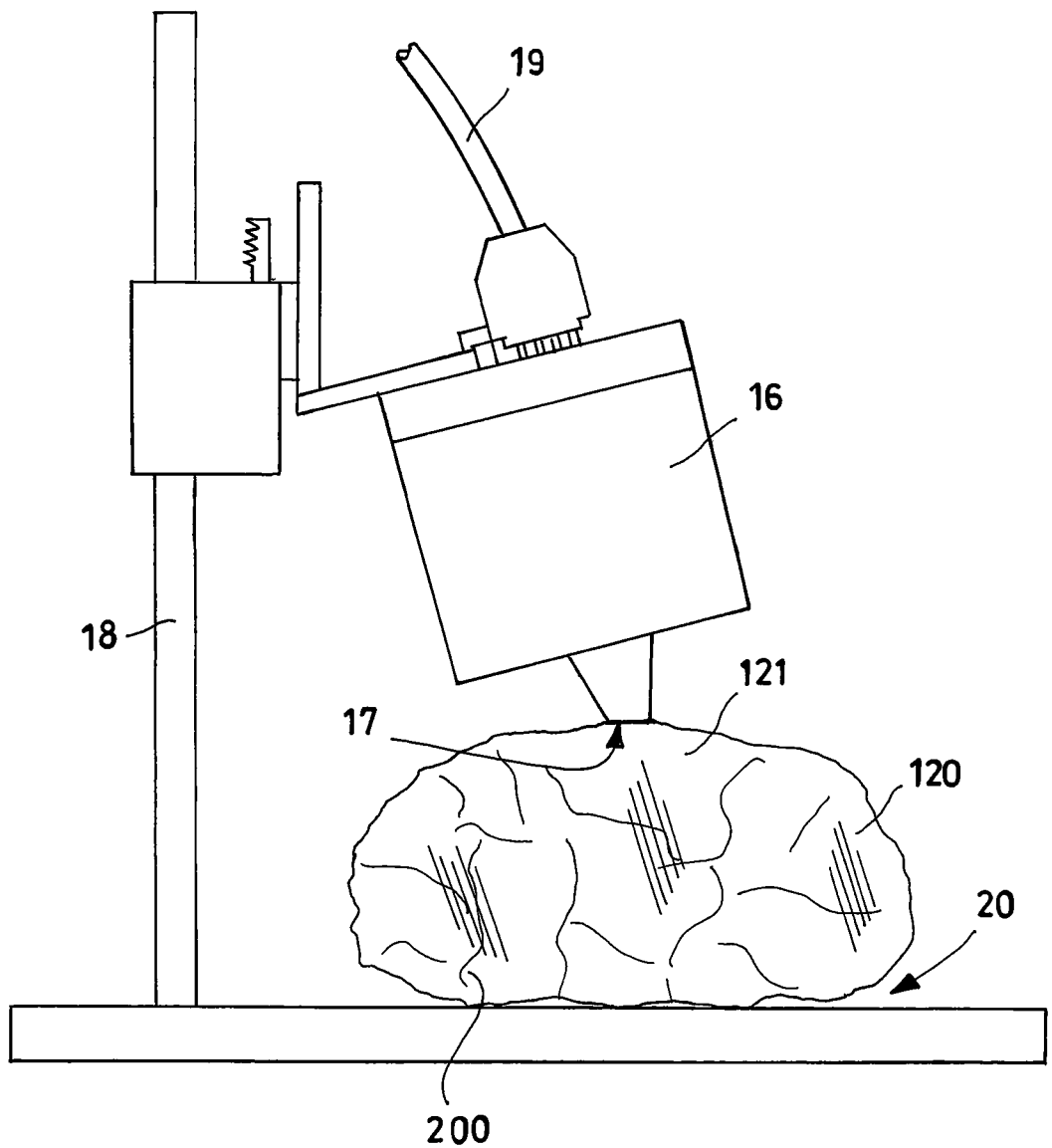
FIG. 2 is an elevational front view of the apparatus for the non-destructive testing of the integrity and/or suitability of sealed packagings of FIG. 1 constrained to a support structure.
Figure 3:
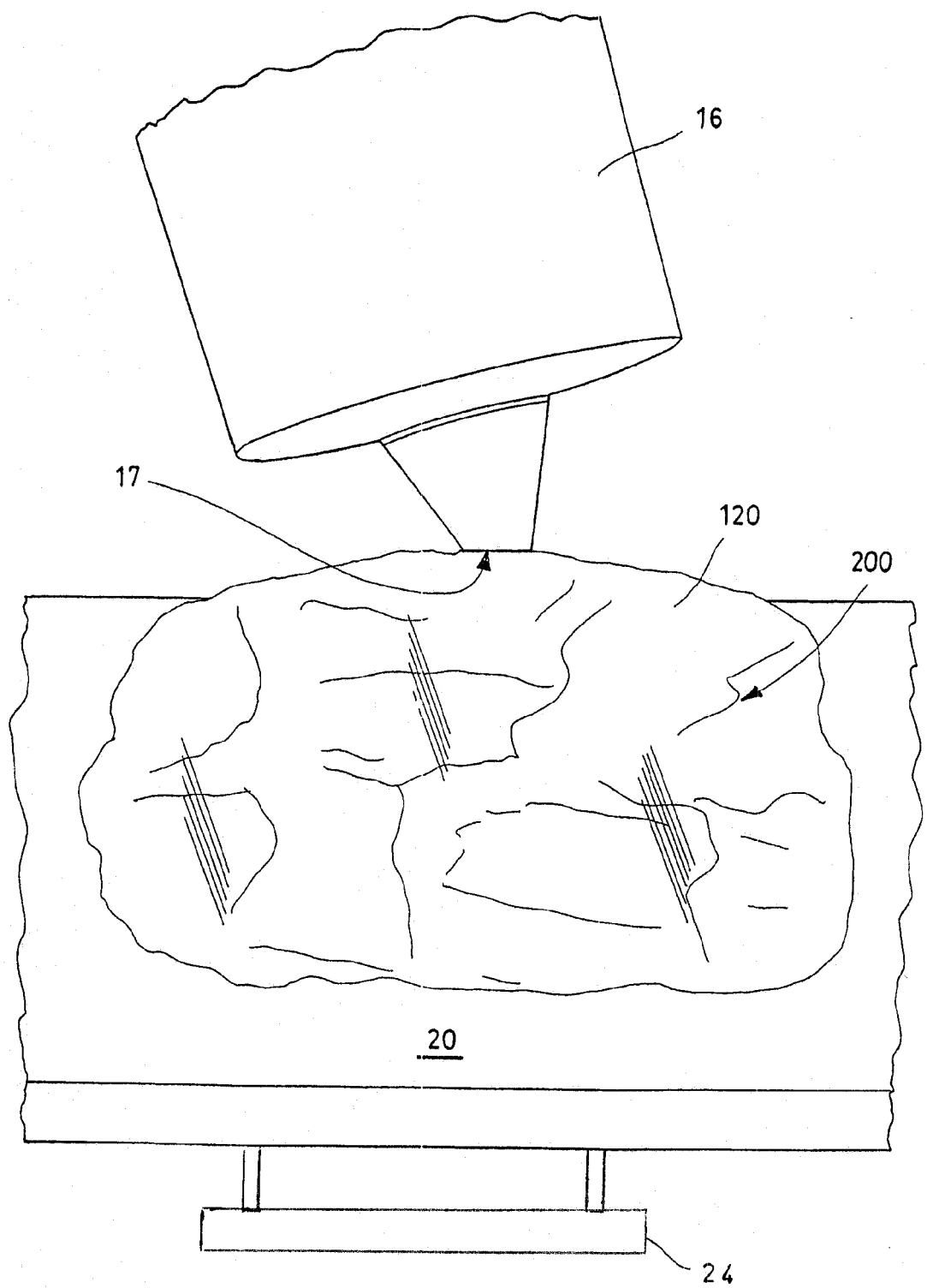
FIG. 3 is an enlarged perspective detail of FIG. 2.

In FIG. 1, the packaging 100 is represented by a container 110 open at the upper part and sealed for example by means of a transparent film 111. In FIGS. 2 and 3, instead, the packaging is represented by a food product bag 120.

In any case, any other type of packaging 100 may be used wherein at least one portion of the material making the outer casing of the packaging itself is at least partially optically transparent.

In the case, for example, of the container 110 open at the upper part, the optically transparent portion is represented by the sealing transparent film 111, while in the case of the food product bag 120, the transparent portion is constituted by at least one portion 121 of the bag itself.

In case of a food packaging 100 at least one food product 200 is generally comprised therein.

The apparatus 10 for the non-destructive testing of the integrity and/or suitability of packagings comprises at least one inspection area 20 suitable for housing the packaging 100.

The inspection area 20 is preferably constituted by a supporting plane or tray.

The apparatus 10 further comprises a laser source 11 having an optical axis A, which can be preferably tuned in frequency to emit a collimated laser beam 12 at a determined wavelength. The wavelength for emitting the laser beam 12 is adjusted so as to substantially coincide with the wavelength for absorbing the gas which is intended to be measured with the aim of obtaining an indication as regards the integrity and/or suitability of the examined packaging 100. For example, should one intend to determine the concentration of oxygen in the packaging 100, the wavelength for adjusting the laser beam is preferably comprised in the range around 760 nm.

The laser source 11 is positioned so as to emit the laser beam 12 towards the at least one inspection area 20, wherein the packaging 100 should be housed in the at least one inspection area 20 with the at least one portion 111,121 thereof at least partially optically transparent faced towards the laser source 11.

The apparatus 10 further comprises a detector 13, preferably a photo-detector, positioned so as to detect an absorption signal of at least one portion of back-scattered beams 12' following the collision of the laser beam 12 emitted by the source 11 with the target constituted by the bottom of the packaging 100 or by the food product 200 or any other element contained therein.

In particular, the detector 13 determines a signal for indicating the occurred absorption due to the passage of the laser beam 12 and the back-scattered beams 12' through the atmosphere inside the container 100, comprising the gas subject of the measurement.

The detector 13 is also such to provide—at the output—a representative datum of the absorption spectrum of such gas present in the atmosphere inside the container 100 on the basis of the detected back-scattered beams 12'.

For the conveying of the back-scattered beams 12' towards the detector 13 there is preferably provided a special collimation optical system 14 which preferably comprises a mirror 14a and a collimation lens 14b having a focal axis B, suitable for focusing on the detector 13 at least part of the back-scattered beams 12'.

This allows positioning the laser source 12 and the detector 13 on the same side, thus allowing performing a measurement of the absorption signal even in packagings 100 having a portion 111,121 at least partially optically transparent on one side alone.

Furthermore, the detection of the absorption signal occurs on a set of beams 12,12' that has performed a double passage through the free space inside the packaging 100, traversing the mixture of gases contained therein twice and thus increasing the path of the beam in the mixture of gases and thus the measurement precision.

As known in the industry, the intensity of a monochromatic light beam which traverses an absorption means is a function of the wavelength thereof and the route path, in particular according to the following law:

$$I(\lambda, z) = I(\lambda, 0) \cdot \exp[-k(\lambda) \cdot z]$$

where $k(\lambda)$ is a positive constant referred to as the coefficient of absorption which, according to the law of Beer, is proportional to the concentration of the absorbing material.

Therefore, determining the concentration of the gas in question indicating the integrity and/or suitability of the packaging 100 requires accurately knowing the overall travel covered by the laser beam 12 and by the set of back-scattered beams 12' within the packaging 100.

According to the present invention, the apparatus 10 further comprises means for measuring the distance covered by the laser beam 12 and by the set of back-scattered beams 12' in the packaging 100.

According to a preferred embodiment, the means for measuring the distance covered comprise a triangulation system.

Specifically, the triangulation system is obtained by using a video camera 15, for example of the CCD type, positioned so as to focus the inspection area 20.

In particular, the light spot generated by the laser beam 12 on the target (the bottom of the packaging 100 or the struck food product 200) identifies the point with respect to which the measurement of the distance is carried out.

The position of such light spot inside the area framed by the video camera 15 provides an indication of the angle between the line joining the video camera 15 and the light spot and the vertical.

Given that the relative position between the video camera 15 and the laser source 11 is known, as well as the inclination of the laser beam 12 emitted by the same 11, the indication regarding the aforementioned angle allows accurately calculating the distance between the laser source 11 and the target.

In addition there are also provided electronic processing means (not illustrated) which, on the basis of the representative datum of the absorption spectrum of the monitored gas and the measured distance accurately determine the concentration of such gas.

In the case of monitoring the concentration of oxygen as the gas indicating the integrity and/or suitability of the packaging 100, it is required that the entire optical path be placed in an atmosphere substantially without oxygen with the aim of shielding the signal produced by the absorption in the packaging 100 with the signal coming from the oxygen present in the atmosphere, the latter generally being considerably stronger than the former.

For such purpose, the laser source 11 and the detector 13 possibly alongside the collimation optical system 14 are positioned inside a containment chamber 16 from whose internal gaseous environment oxygen is removed.

The removal of oxygen is obtained by way of example by introducing into the containment chamber 16 one of more substances capable of either chemically or physically subtracting oxygen from the environment, such as for example iron dust which has a spontaneous tendency to chemically bond to oxygen forming rust.

The containment chamber 16 preferably comprises a window 17 suitable for resting on the at least one portion 111,121 at least partially optically transparent of the packaging 100.

The plane in which the window 17 lies and the optical axis A of the laser source 11 are inclined one with respect to the other by an angle preferably comprised between 10° and 20° and, even more preferably equal to about 15°, to avoid spurious reflections by a portion of the packaging 111,121 on which the laser beam 12 is incident which would interfere with the laser beam 12.

Actually a reflection by a portion of the packaging 111,121 on which the laser beam 12 is incident would cause on the detector 13 a radiation which has not traversed the oxygen inside the packaging 100, altering the measurement.

Still in case of monitoring the concentration of oxygen, the apparatus 100 operates preferably in digital modulation regime of the wavelength (dWMS) for increasing the measurement sensitiveness.

Actually, the measurement of the oxygen is characterized by weak absorption lines in the absorption region (around 760 nm) thereof.

The laser source 11 and the detector 13, possibly alongside the collimation optical system 14, are preferably mounted on a frame 18, possibly through the interposition of the containment chamber 16.

Preferably, the laser source 11, the detector 13 and, if present, the collimation optical system 14 are constrained to the mounting frame 18 in a moveable manner, so as to allow adjusting the respective vertical positioning.

Furthermore there are provided interface means 19, for the connection of the laser source 11 and the detector 13 to said electronic processing means which, besides calculating the concentration of the monitored gas, are preferably suitable for guiding the activation of the apparatus 100 according to the present invention.

With the aim of further reducing the interferential effects associated to the optical path there are present vibrating means 23 associated to the collimation lens 14b of the back-scattered beams 12' and/or associated to the supporting plane or tray defining the inspection area 20.

Such vibrating means, for example constituted by vibrator motors of the known unbalanced flywheel type, revealed to be useful for the destruction of the geometric coherence on subsequent means of the optical paths due to parasite reflections.

Preferably, first vibrating means 23 are such to generate an oscillating displacement of the collimation lens 14b of the back-scattered beams 12' on a plane perpendicular to the incident laser beam 12 on the detector 13, i.e. to the focal axis B of the collimation lens 14b, thus obtaining a minimum variation of the direction of the laser beam 12 sent on the target 100,200.

For such purpose, the collimation lens 14b is mounted on a support 21 equipped with an elastic joint 22, to which there is associated a vibrator motor 23.

Figure 4:
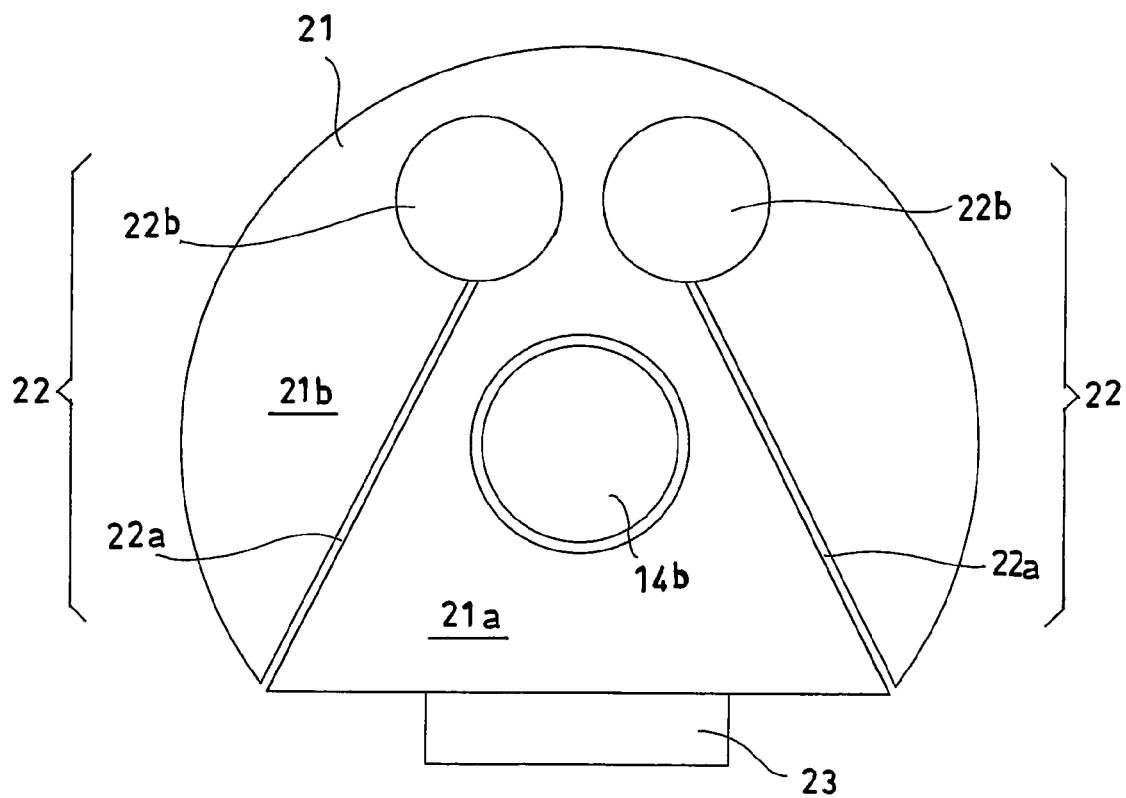
FIG. 4 is a schematic representation of the support of the collimation lens inside an apparatus for the non-destructive testing of the integrity and/or suitability of sealed packagings according to the present invention.

The elastic joint 22 may for example be directly obtained in the lens holder support by providing two notches 22a ending in respective holes 22b, as shown in FIG. 4.

In such preferred embodiment, the vibrator motor 23 transfers to the support portion 21a which carries the collimation lens 14b an oscillation movement with respect to the remaining part of the support 21b, along a plane transverse to the focal axis B of the collimation lens 14b.

Alternatively or additionally, there are provided second vibrating means 24 capable of generating a vertical shift of the supporting plane or tray defining the inspection area 20.

The oscillation of the supporting plane or tray 20 is particularly efficient for reducing the etalon effect which forms between the beams scattered by the at least one portion 111, 121 at least partially optically transparent of the packaging 100 and by the target 100,200, varying the relative distance between the same.

Due to the introduction of the vibrating means described above, the difference of optical path is mechanically modulated and when the spectrum is mediated, the etalon effect is substantially nullified.

The apparatus for the non-destructive testing of the integrity and/or suitability of sealed packagings 100 operates as follows.

When the apparatus for the non-destructive testing of the integrity and/or suitability of packagings 100 is activated, the laser source 11 sends a laser beam 11 towards an inspection area 20 in which has been housed a packaging 100 so that the at least one portion 111,121 thereof, at least partially optically transparent, is faced towards the laser source 11.

The laser beam 12 penetrates into the packaging through the at least one portion 111,121, at least partially optically transparent, and is incident on a target which can be constituted by the bottom of the packaging 100 or by the content thereof, such as for example a food product 200.

The light spot that the laser beam 12 generates on the target is detected by the triangulation system 15 which determines the distance thereof from the laser source 11.

The back-scattered beams 12' which are incident on the collimation optical system 14 are focused on the detector 13.

According to the intensity of the beams incident on the detector 13 and the calculated distance there is determined the coefficient of absorption of the particular monitored gas, thus obtaining a measurement proportional to the concentration of such gas.

According to the concentration of the measured gas it is subsequently possible to determine whether the packaging is integral and/or has an atmosphere meeting the expected requirements.

From the description above the characteristics and advantages of the apparatus for the non-destructive testing of the integrity and/or suitability of sealed packagings subject of the present invention are clear.

Actually, the apparatus for the non-destructive testing of the integrity and/or suitability of sealed packagings according to the present invention allows measuring—in absolute terms—the concentration of a gas inside a sealed packaging, thus providing an absolute indication as regards the integrity and/or suitability thereof.

In particular, due to the accurate measurement of the distance, the apparatus according to the present invention is capable of performing absolute measurements of concentration on any type of material, in which the measurement does not depend on the presence or absence of other gases.

Furthermore, such apparatus can be applied both for testing the packagings containing liquids and for controlling packagings containing solids of the food, pharmaceutical, medical type or any other type.

Thus, it is possible to obtain reliable measurements without altering the integrity of the packaging, a characteristic which makes the apparatus according to the present invention entirely suitable for use in line.

Last but not least, such apparatus can be validly implemented also with laser sources of extremely low power (0.3 mW).

Lastly, it is clear that the apparatus for the non-destructive testing of the integrity and/or suitability of sealed packagings thus conceived is susceptible to numerous modifications and variants, all falling within the scope of the invention; furthermore, all details can be replaced by technically equivalent elements.

In particular, though an apparatus for the non-destructive testing of the integrity and/or suitability of sealed packagings according to the present invention has been described by way of example in relation to the measurement of oxygen, it is clear that it can be used for analyzing other gases such as water vapour, carbon dioxide or other gases of particular interest in the food, pharmaceutical or medical industry.

Therefore, though being particularly used in the food industry, such apparatus can also advantageously be used for the non-destructive testing of the integrity and/or suitability of packagings for pharmaceutical or medical products.

Furthermore, it can also be used in anti-fraud applications, in which the alteration of the oxygen concentration is considered tampering with the sealing.

Furthermore, the apparatus for the non-destructive testing of the integrity and/or suitability of sealed packagings according to the present invention is also suitable for the non-invasive measuring of the pressure inside a container containing a sufficient amount of the measured gas, for example an atmosphere with the 21% of oxygen.

The pressure measurement is carried out by evaluating the extension of the spectral line caused by the impacts of the molecules and thus the function of the pressure.

In practice all materials used, as well as the dimensions, may vary according to the technical requirements.

The invention claimed is:

1. An apparatus (10) for the non-destructive testing of the integrity or suitability of sealed packages (100) having at least one portion (111, 121) at least partially optically transparent, comprising:
   at least one inspection area (20) suitable for housing said packaging (100);
   at least one laser source (11) with an optical axis (A) for the emission of a laser beam (12) at a wavelength substantially coinciding with a gas absorption wavelength, said at least one laser source (11) being positioned so as to direct said laser beam (12) towards said at least one inspection area (20);
   at least one detector (13) positioned so as to detect at least a portion of retro-scattered beams (12') following the collision of said laser beam (12) emitted from said laser source (11) with a target (100,200) and provide, at the output, data representing an absorption spectrum of said gas; characterized in that it comprises measurement means of a distance covered by said laser beam (12) and by said at least one portion of backscattered beams (12') inside said packaging (100) and electronic processing means for calculating the concentration of said gas on the basis of said data representing said absorption spectrum and said distance covered wherein a collimation optical system (14) is associated with said detector (13) of at least a portion of said backscattered beams (12') towards said detector (13) and wherein said collimation optical system (14) comprises a mirror (14a) and a collimation lens (14b) having a focal axis (B), suitable for focusing a portion of said backscattered beams (12') on said detector (13) and wherein said apparatus comprises first vibrating means (23) associated with said collimation lens (14b) of said backscattered rays (12').

2. The apparatus (10) for the non-destructive testing of the integrity or suitability of sealed packages (100) according to claim 1, wherein said measurement means of the distance covered comprise a triangulation system.

3. The apparatus (10) for the non-destructive testing of the integrity or suitability of sealed packages (100) according to claim 2, wherein said triangulation system comprises a video camera (15) positioned so as to frame said inspection area (20).

4. The apparatus (10) for the non-destructive testing of the integrity or suitability of sealed packages 100) according to claim 1, wherein said laser source (11) and said detector (13) are positioned inside a containment chamber (16) having a substantially oxygen-free gaseous environment.

5. The apparatus (10) for the non-destructive testing of the integrity or suitability of sealed packages (100) according to claim 4, wherein said containment chamber (16) comprises in its interior, at least one substance capable of either chemically or physically subtracting oxygen from the environment.

6. The apparatus (10) for the non-destructive testing of the integrity or suitability of sealed packages (100) according to claim 4, wherein said containment chamber (16) comprises a window (17) suitable for resting on said at least one portion (111,121) at least partially optically transparent, of said packaging (100), the plane on which said window (17) lies being tilted with respect to said optical axis (A) of said laser source (11) by an angle of between 10° and 20°.

7. The apparatus (10) for the non-destructive testing of the integrity or suitability of sealed packages (100) according to claim 4, wherein said containment chamber (16) comprises a window (17) suitable for resting on said at least one portion (111,121) at least partially optically transparent, of said packaging (100), the plane on which said window (17) lies being tilted with respect to said optical axis (A) of said laser source (11) by an angle of about 15°.

8. The apparatus (10) for the non-destructive testing of the integrity or suitability of sealed packages (100) according to claim 1, wherein said laser source (11) and said detector (13) are movably constrained to a frame (18).

9. The apparatus (10) for the non-destructive testing of the integrity or suitability of sealed packages (100) according to claim 1, wherein said collimation lens (14*b*) is assembled on a support (21) equipped with an elastic joint (22), said first vibrating means (23) being associated with said elastic joint (22).

10. The apparatus (10) for the non-destructive testing of the integrity or suitability of sealed packages (100) according to claim 9, wherein said elastic joint (22) is formed in said lens-holder support (21) and said lens-holder comprises a pair of notches (22*a*) ending in respective holes (22*b*).

11. The apparatus (10) for the non-destructive testing of the integrity or suitability of sealed packages (100) according to claim 1, wherein said apparatus (10) includes a second vibrating means associated with a supporting plane or tray defining said inspection area (20), suitable for generating a vertical shift of said supporting plane or tray (20).

12. The apparatus (10) for the non-destructive testing of the integrity or suitability of sealed packages (100) according to claim 1, which is operated under a digital modulation regime of the wavelength (dWMS).

\* \* \* \* \*